(12) United States Patent
Kawasaki et al.

(10) Patent No.: US 6,333,151 B2
(45) Date of Patent: *Dec. 25, 2001

(54) NUCLEIC ACID MARKERS FOR RICE BLAST RESISTANCE GENES AND RICE BLAST RESISTANCE GENES ISOLATED BY THE USE OF THESE MARKERS

(75) Inventors: Shinji Kawasaki; Masaya Satoh; Naoki Katsura, all of Ibaraki; Akira Saitoh, Kumamoto; Ikuo Andoh, Ibaraki, all of (JP)

(73) Assignees: Research Development Corporation of Japan, Saitama; National Institute Agrobiological Resources Ministry of Agriculture Forestry and Fisheries, Ibaraki, both of (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/282,557

(22) Filed: Jul. 29, 1994

(30) Foreign Application Priority Data

Jul. 29, 1993 (JP) .................................................... 5-188545

(51) Int. Cl.[7] .............................. C12Q 1/68; C12P 19/34; C07H 21/04; C07H 21/02

(52) U.S. Cl. .............................. 435/6; 435/91.2; 536/24.3
(58) Field of Search ...................... 435/6, 91.2; 536/23.1, 536/24.3, 24.33

(56) References Cited

U.S. PATENT DOCUMENTS 5,674,993 * 10/1997 Kawasaki et al. .................. 536/23.6

OTHER PUBLICATIONS

Saito et al., Jpn. J. Breed. 41:665–670, 1991.*
Yu et al., Theor. Appl. Genet. 81:471–476, 1991.*

* cited by examiner

Primary Examiner—Stephanie Zitomer
(74) Attorney, Agent, or Firm—Wenderoth, Lind & Ponack, L.L.P.

(57) ABSTRACT

The present invention provides nucleic acid markers for rice blast resistance genes Pi-ta and Pi-ta$^2$, which hybridize with any RFLP probes isolated from rice genomic DNA and are located within a distance of 2.0 cM from rice blast resistance genes Pi-ta or Pi-ta$^2$. According to the present invention, it becomes possible to easily identify rice blast resistance genes and related genes from rice cultivars containing Pi-ta or Pi-ta$^2$, thus promoting development and breeding of superior cultivars. It becomes also possible to easily carry out a resistance test of rice. This will open up way to create new resistance genes.

3 Claims, 3 Drawing Sheets

NUCLEIC ACID MARKERS FOR RICE BLAST RESISTANCE GENES AND RICE BLAST RESISTANCE GENES ISOLATED BY THE USE OF THESE MARKERS

This application claims priority under 35 USC 119 from Japanese patent application 188545/1993 filed Jul. 29, 1993.

BACKGROUND OF THE INVENTION

1. Field of the Invention

The present invention relates to nucleic acid markers for rice blast resistance genes, and rice blast resistance genes isolated by using these nucleic acid markers.

The rice blast resistance genes are very useful not only for the development of superior cultivars of rice, but also as a material for research and a genetic resource for creating new resistance genes capable of being introduced into various plants.

2. Description of the Related Art

It is well known that there are genes rendering resistance against pathogens to plants, and introduction of these genes has been an important target in the conventional breeding efforts. As a result, many new types of cultivars have been created to date through introduction of these resistance genes. Importance of these resistance genes will further increase throughout the world since such biotic methods utilizing the innate functions of plants to prevent epidemics will lower consumption of chemical pesticides, promote human health, protect the environment while still lowering the cost of agriculture.

Among the plant resistance genes against pathogens, the rice blast resistance gene was first discovered in Japan, and the presence of many such genes has since been discovered. In particular, resistance genes derived from indica rice exhibit resistance to many strains of the rice blast fungi found in Japan, and are highly useful as genetic resources. Among others, Pi-ta and Pi-ta$^2$ genes derived from indica rice are suited for RFLP mapping of the genes. There are however still only a very limited number of cases of actual introduction of these resistance genes into present elite cultivars.

The probable reasons are that the conventional breeding method requires many generations of backcrosses to introduce a resistance gene into a cultivar, accompanied with resistance tests by inoculating pathogens to many individuals every year. Application of a resistance test to pathogens of foreign-origin is almost impossible within Japan because of the strict control over the importation of foreign pathogens.

On the other hand, recent progress in plant biotechnology has enabled the identification and isolation of various genes, and the introduction of them into other plants. Therefore, for plant resistance genes also, it is not difficult to introduce them into any desired cultivar by genetic engineering techniques if it was cloned. Further, it will drastically reduce the time and labor required for breeding resistant cultivars. It will also be possible to clarify the mechanism about how the resistance genes work in plants, and make possible modifications to the present gene and then provide new types of resistance genes. Many research groups are now making efforts to isolate resistance genes, but only a few have been successful to date. This is attributable to the fact that there is only limited information about the biochemical character of the resistance gene-products.

As a method for identifying and isolating genes, a technique known as positional cloning is now attracting attention. This technique uses nucleic acid markers near a target gene in a genome map, and isolates target genes from a genome library. Actually, some genes causing human hereditary diseases have been isolated by the application of this technique.

Although only a few cases of success of this positional cloning have been reported in plants, rice is considered to be the most suited plant for this technique for the following reasons: (1) rice has the smallest genome size among the major crops; (2) physical distance (in kb) corresponding to an unit genetic distance (cM) is very small in rice; (3) it is easy to limit the range of the gene location by utilizing several near isogenic lines (NIL) which have been developed by introgressing the indica derived genes into japonica backcross; and (4) it is easy to introduce genes into cells for a complementation test.

An important key to success of this positional cloning is whether or not good adjacent markers are available. Calculating from the rice genome size and the genetic map, the physical distance corresponding to 1 centiMorgan (cM) of the rice genetic map is estimated to be about 100–200 kb on a nucleic acid basis. On the other hand, the average size of the insert of yeast artificial chromosome (YAC) is more than 200 kb. Therefore, if there is a DNA marker for the resistance genes within a distance of 100 kb, i.e., 0.5–1 cM, the possibility of success of positional cloning of the gene is considered to be very high.

Such nearby nucleic acid markers of rice blast resistance genes would be also useful for largely reducing the time and labor required for testing resistance in conventional breeding through backcrosses, for example.

SUMMARY OF THE INVENTION

It is an object of the present invention to provide novel nearby nucleic acid markers of rice blast resistance genes, and rice blast resistance genes isolated and cloned by the use of these markers.

The present invention provides nuclei acid markers of rice blast resistance genes, which hybridize with any RFLP probes isolated from rice genomic DNA and are located within a distance of 2.0 centiMorgan (cM) from rice blast resistance gene Pi-ta or Pi-ta$^2$.

The present invention also provides secondary nucleic acid markers located near the above-mentioned nucleic acid markers of rice blast resistance gene, and a genes group associated with them isolated by use of those nucleic acid markers.

According to the present invention, good markers for rice blast resistance genes Pi-ta$^2$ or Pi-ta are provided. By the use of these nucleic acid markers, it becomes possible to easily isolate rice blast resistance genes and related gene groups from various cultivars of rice, thus promoting development and breeding of superior cultivars. It is also possible to easily carry out a resistance test of rice. This will open up the way to create new resistant genes.

BRIEF DESCRIPTION OF THE DRAWINGS

FIG. 3a: F$_2$ analysis of the crossing between Pi No. 4 (with Pi-ta$^2$) and Norin 22 (without Pi-ta$^2$). FIG. 3b: F2 analysis of the crossing between Kasalath (indica) and Koshihikari (japonica); both are without resistance gene. FIG. 3c: The possible region of Pi-ta$^2$ derived from the results of FIG. 2. The smaller bracket indicates the case with Pi-ta and Pi-ta$^2$ are strictly allelic. The larger bracket indicates the case when Pi-ta and Pi-ta$^2$ are not strictly allelic.

DETAILED DESCRIPTION OF THE INVENTION

Figure 1:
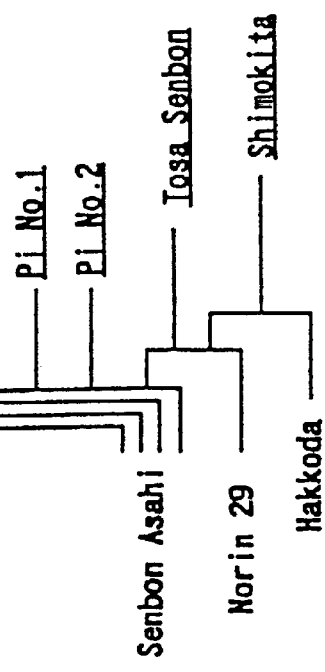
FIG. 1 is a pedigree illustrating the introduction of rice blast resistance genes Pi-ta and Pi-ta$^2$ into japonica rice cultivars. Underlines indicate cultivars with the resistance genes.
Figure 1:
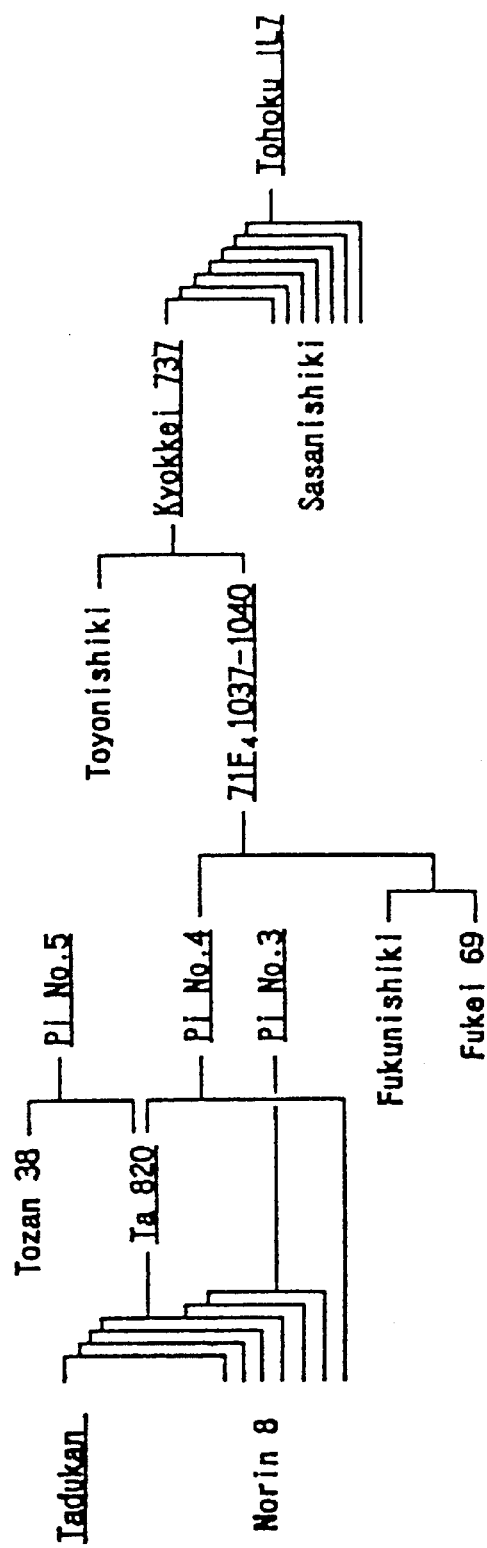

The nucleic acid markers of the present invention are described further in detail below.

The nucleic acid markers of the present invention are obtained by comparing genomic DNAs of several different cultivars of rice with blast resistance gene Pi-ta or Pi-ta$^2$ and those of rice cultivars without blast resistance genes, and identifying a specific DNA band present only in cultivars with rice blast resistance genes in the neighborhood (within 2.0 cM or 200–400 kb) of a rice blast resistance gene.

Comparison of genomic DNAs can be conducted between indica rice cultivars (donor parent) having rice blast resistance genes, and japonica rice cultivars (recurrent parent) not having such genes, and between rice cultivars of near isogenic lines developed by recurrent crossing of the donor parent and the recurrent parent.

Furthermore, the nucleic acid marker of the present invention can be detected by hybridizing with any RFLP probes. In the present invention, therefore, identification of a DNA marker can be accomplished by cleaving the genomic DNA of the rice cultivar to be tested (for example, the above-mentioned donor parent, recurrent parent, and near isogenic lines) with restriction enzyme, and then hybridizing an RFLP probe after gel electrophoresis.

The nucleic acid marker of the present invention thus made available can be differentiated by RFLP analysis to be indica or japonica origin in the genomic DNA of a test individual rice cultivar, and are located within the neighbourhood of 2 cM of the rice blast resistance genes Pi-ta or Pi-ta$^2$, and serve as a good marker of a rice blast resistance gene or related gene.

The present invention will be described below further in detail by means of Example and Tests.

EXAMPLE AND TESTS

Example

Nucleic acid markers of the rice blast resistance gene Pi-ta$^2$ were identified.

(1) Preparation of Materials (a) DNA Extract:

The following extracts were prepared by known methods, respectively:

1) *Escherichia Coli* plasmid DNA containing a rice DNA library;
2) DNA of a rice cultivar (donor parent) having a rice blast resistance gene Pi-ta$^2$;
3) DNA of a japonica rice cultivar (recurrent parents) not having the rice blast resistance gene Pi-ta$^2$;
4) DNA of rice cultivars (near isogenic lines) developed by repeating crossing the recurrent parents to the donor parents.

(b) RFLP Probe:

RFLP probes of the rice twelfth chromosome specified by Saito et al. (Jpn. J. Breed., 41, 665–670, 1991) are used.

(2) Hybridization of DNA Fragments and RFLP Probes

For each of the DNA extracts 1) to 4) listed under (a) above, 2–3 μg of the genomic DNA was fragmented by the use of restriction enzyme (see Table 1), and added to 3–5×1-mm gelslot of 0.7–1% agarose with 1×TAE buffer and electrophoresed at the voltage gradient of 5 V/cm for four hours. Then, DNA was transferred from the electrophoresed gel to a nylon membrane by a known technique. On the other hand, the RFLP probe listed above in (b) was labeled with $^{32}$p or peroxidase by a known technique (the random primer method, for example), and was specifically hybridized to the DNA fixed to the membrane through their complementarity by the Southern hybridization method. Subsequently, the hybridied DNA band was detected through exposure to X ray films.

(3) Identification of Nucleic Acid Markers:

For the DNA fragments of the DNA extracts listed under (2), (3), (4) of (1)-(a) above, DNA bands hybridized with the RFLP probes were compared, and bands which were present in the DNAs 2) and 4) having rice blast resistance genes Pi-ta$^2$ but not present in the DNA 3) not having the gene Pi-ta$^2$ were marked. And the DNA bands located within a distance of 2.0 cM from the genes Pi-ta$^2$ were selected from these DNA bands by F$_2$ analysis, and the DNA bands were identified as the nucleic acid markers of the gene Pi-ta$^2$.

Table 1 shows RFLP probes hybridized with the nucleic acid markers in the neighborhood of Pi-ta$^2$, their sizes and restriction enzymes used to cleave the genomic DNA.

TABLE 1

| Nucleic acid markers | size(kb) | Restriction Enzyme |
| --- | --- | --- |
| XNpb261 | 1900 | BgIII |
| XNpb088 | 1540 | EcoRV |
| XNpb154 | 990 | HindIII |
| XNpb239-1 | 980 | HindIII |
| XNpb289 | 730 | EcoRV |
| XNpb196 | 490 | EcoRV |
| XNpb319 | 750 | BgIII |
| RUB$_{SS}$ | 700 | EcoRV |
| XNpb316 | 2300 | EcoRV |

It was also confirmed that these markers are also applicable as satisfactory marker of Pi-ta$^2$ for rice genome libraries 1) above if these were derived from rice cultivars having genes Pi-ta$^2$.

Next, some Tests carried out to investigate characteristics of these nucleic acid markers will be shown.

Test 1

For the nucleic acid markers obtained in Example, the behavior thereof was tested in near isogenic lines (NILs) into which rice blast resistance genes were introduced by repeated backcrosses from an indica rice cultivar.

Pi-ta$^2$ and Pi-ta genes derived from a indica rice are known to occupy the same locus and are introduced into five and four lines, respectively, through repeated backcrosses as shown in FIG. 1. RFLPs near Pi-ta$^2$ were investigated in these donor parents, recurrent parents and near isogenic lines, and the chromosome region derived from indica rice were clarified for each cultivar.

DNAs were extracted from each of the cultivars shown in FIG. 1 to carry out Southern blots using the RFLP probes shown in Table 1 and to investigate the chromosome region derived from indica rice in each of near isogenic lines (FIG.

Figure 2:
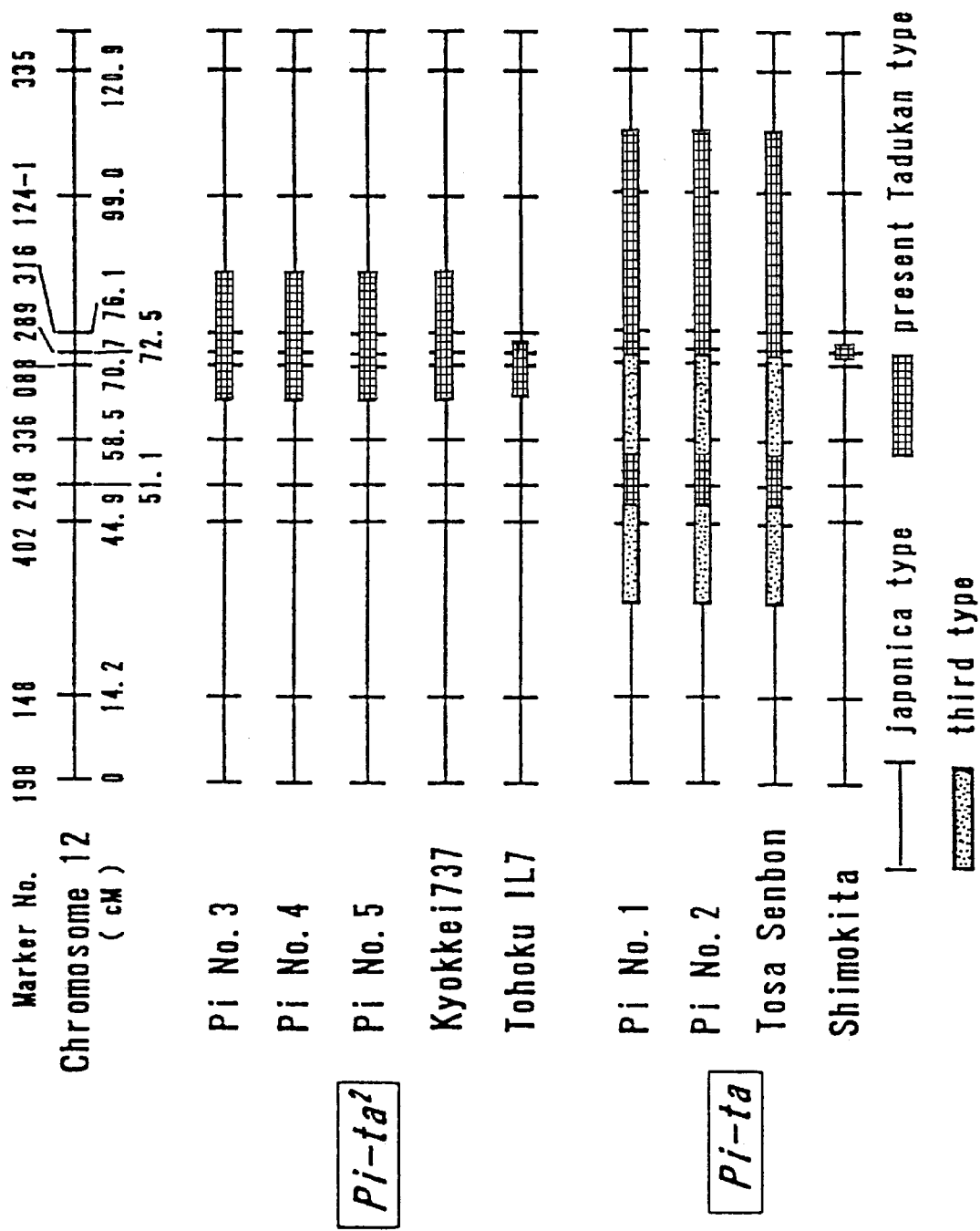
FIG. 2 is a schematic view illustrating the rice twelfth chromosome of the near isogenic lines having the Pi-ta$^2$ or Pi-ta gene. Black or gray parts indicate the region derived from indica donor.

2). As a result, the position of Pi-ta$^2$ on the chromosome map was estimated to be within the batched range in FIG. 2.

Test 2

An $F_2$ analysis was carried out to locate the rice blast resistance gene Pi-ta$^2$ in the RFLP map.

PiNo. 4, a cultivar having the rice blast resistance gene Pi-ta$^2$, and Norin 22, a cultivar not having Pi-ta$^2$ were crossed, and many $F_2$ individuals were obtained. Using these $F_2$, recombination ratio between the rice blast resistance gene Pi-ta$^2$ and the nucleic acid markers were determined, and the hereditary distances between them were determined.

About 400 grains of $F_2$ individuals were grown, and at about the five-leaf period, a suspension of rice blast strain Hoku-1 conidia of $1\times10^5$/ml was spray-inoculated to the leaves. The inoculated leaves were left at 25 °C., relative humidity of 100% for 24 hours, then brought to a greenhouse. After 7 days from inoculation, resistant and susceptible individuals were diagnosed from the occurrence of necrotic lesions on the leaves.

Figure 3A:
FIGS. 3a–3c provide a schematic view of the rice twelfth chromosome enlarging the locus of rice blast resistance genes Pi-ta$^2$ and Pi-ta.
Figure 3B:
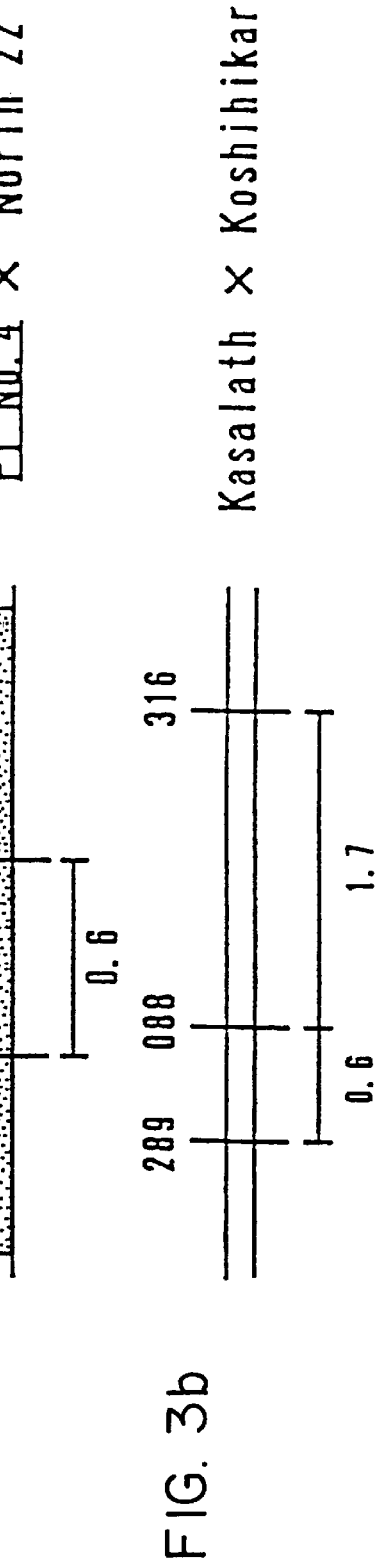
Figure 3C:
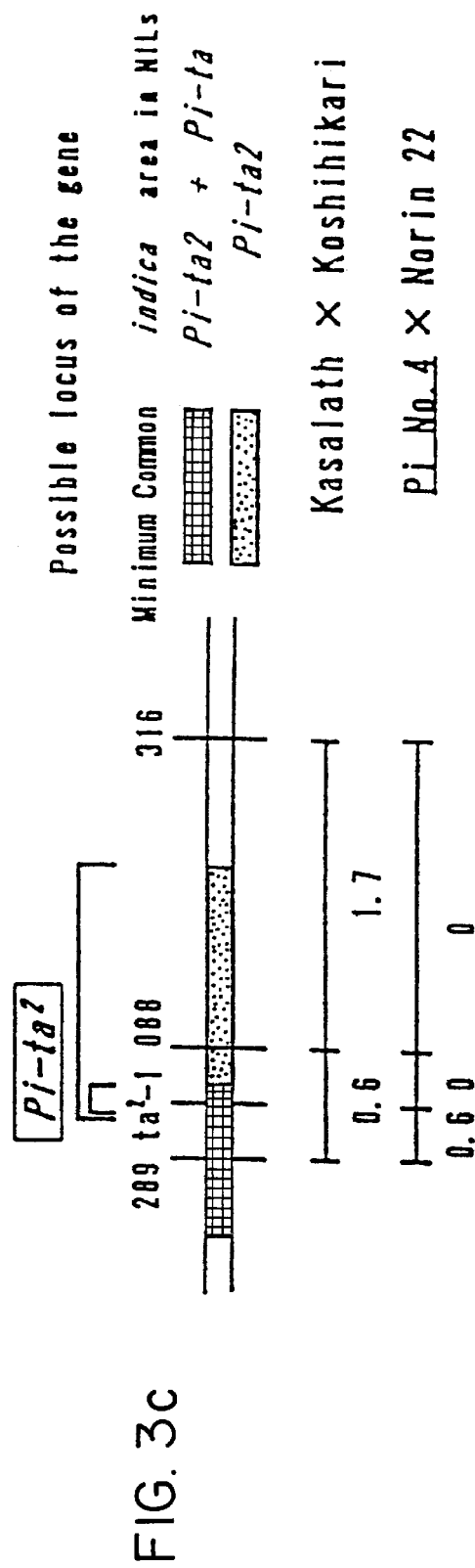

DNA was extracted from each of 84 individuals determined to be susceptible, and a Southern hybridization was carried out with the RFLP probes in the same manner as the Example, to test whether each nucleotide marker band was of the indica type or of the japonica type. As a result, no recombination was found with the nucleic acid marker probed with XNpb289, and the genetic distance between the marker and the resistance gene was estimated to be 0.6 cM. This distance corresponds to a distance of under about 60–120 kb for genomic DNA. This is a very short distance considering the easy availability of 200 to 300 kb genome fragments in yeast artificial chromosome (YAC). Positional cloning will be sufficiently possible for this distance. As the other nucleic acid markers hybridized with the other probes are located within a distance of 2 cM on the map, it is suggested that these nucleic acid markers serve as good markers for Pi-ta$^2$ gene (FIG. 3).

Only susceptible individuals were used in the $F_2$ analysis to avoid occurrence of susceptible individuals apparently showing no lesion and diagnosed to be resistance, due to insufficient spray-inoculation. In contrast, the possibility that a resistant individual show many necrotic lesions is very low. This consequently leads to a higher accuracy for the diagnosis of the phenotype. As the resistance genes are dominant, susceptible individuals are recessive homos of the japonica type at the loci of genes Pi-ta$^2$, and the band patterns of markers in the neighborhood are expected to be of the japonica type. Therefore, even one recombination of the two homologous chromosomes to the indica type can be easily detected. As it is possible to detect recombinations in twice numbers of chromosomes of individuals, efficiency of measurement of the recombination ratio becomes also twice as high. These two advantages are very important for determining the distance between two genes of very low recombination ratio.

From the results of Tests 1 and 2 described above, it was confirmed that the nucleic acid markers obtained in Example was a satisfactory labeling marker for genes Pi-ta and Pi-ta$^2$, locating within a distance of 0 to 2 cM on the genetic map from rice blast resistance genes Pi-ta and Pi-ta$^2$.

What is claimed is:

1. A method for identifying a rice genomic region of the rice blast resistance gene Pi-ta or Pi-ta$^2$, which comprises:

digesting rice genomic DNA with enzymes selected from the group consisting of Bgl, EcV and Hin, to obtain rice genomic DNA fragments, hybridizing the rice genomic DNA fragments with RFLP probes selected from the group consisting of XNpb289, XNpb196, XNpb319, XNpb239-1, XNpb154, XNpb88, XNpb261, RUBss and XNpb316, identifying the rice genomic DNA fragments on which the RFLP probes hybridize as nucleic acid markers for the rice genomic region of the rice blast resistance gene Pi-ta or Pi-ta$^2$, and identifying the rice genomic region of the rice blast resistance gene Pi-ta or Pi-ta$^2$ with the nucleic acid markers.

2. The method according to claim 1, wherein each of the RFLP probes hybridizes to the rice genomic DNA fragments within a distance of 2.0 centiMorgan from the rice blast resistance gene Pi-ta or Pi-ta$^2$.

3. A method for identifying a nucleic acid marker for the rice genomic region of the rice blast resistance gene Pi-ta or Pi-ta$^2$, which comprises:

digesting rice genomic DNA with enzymes selected from the group consisting of Bgl, EcV and Hin, to obtain rice genomic DNA fragments, hybridizing the rice genomic DNA fragments with RFLP probes selected from the group consisting of XNpb289, XNpb196, XNpb319, XNpb239-1, XNpb154, XNpb88, XNpb261, RUBss and XNpb316, and identifying the rice genomic DNA fragments on which the RFLP probes hybridize as nucleic acid markers for the rice genomic region of the rice blast resistance gene Pi-ta or Pi-ta$^2$.

\* \* \* \* \*